(12) United States Patent
Meesilpa et al.

(10) Patent No.: US 7,314,851 B2
(45) Date of Patent: Jan. 1, 2008

(54) SILK SOAP COMPRISING SERICIN PROTEIN

(75) Inventors: Prateep Meesilpa, Bangkok (TH);
Parn Pannengpet, Bangkok (TH);
Pojana Werasopon, Bangkok (TH);
Chanya Pannengpet, Bangkok (TH);
Danai Narkprasert, Bangkok (TH);
Boonya Sudatis, Bangkok (TH);
Wachiraporn Pewlong, Bangkok (TH);
Malee Bunjob, Nonthaburi (TH);
Piyawan Boocha, Nonthaburi (TH);
Pattamawadee Setakanna, Nonthaburi (TH); Preeya Pinnil, Nonthaburi (TH)

(73) Assignee: The Foundation for the Promotion of Supplementary Occupations and Related Techniques of her Majesty Queen Sirikit, Bangkok (TH)

( * ) Notice: Subject to any disclaimer, the term of this patent is extended or adjusted under 35 U.S.C. 154(b) by 343 days.

(21) Appl. No.: 10/862,893

(22) Filed: Jun. 7, 2004

(65) Prior Publication Data

US 2005/0130857 A1    Jun. 16, 2005

(30) Foreign Application Priority Data

Dec. 11, 2003  (TH) ....................... 088023

(51) Int. Cl.
*A61K 7/00* (2006.01)
(52) U.S. Cl. ...................... 510/130; 510/152; 510/159; 510/481; 510/488
(58) Field of Classification Search .................... None
See application file for complete search history.

(56) References Cited

U.S. PATENT DOCUMENTS

| 5,573,702 A | * | 11/1996 | Bonnechere et al. | ........ 510/417 |
| 6,706,675 B1 | * | 3/2004 | Demson et al. | ............. 510/147 |
| 2006/0052263 A1 | * | 3/2006 | Roreger et al. | ............. 510/141 |

FOREIGN PATENT DOCUMENTS

JP        2002226897    *  8/2002

* cited by examiner

*Primary Examiner*—Necholus Odgen, Jr.
(74) *Attorney, Agent, or Firm*—Ladas & Parry

(57) ABSTRACT

The invention discloses skin cleansing product which includes glycerinated soap and hard soap which comprises sericin protein from Thai silk, as a main ingredient, admixed with various components in the soap mass. The present products are safe for use and help nourish the skin so as to smooth and soften the skin when used. The product does not cause irritation and therefore can be used for unisex and all ages.

2 Claims, No Drawings

SILK SOAP COMPRISING SERICIN PROTEIN

SUMMARY OF THE INVENTION

The invention is directed to a skin cleansing product which contains silk protein as a main ingredient. When used regularly, it assists nourish and soften the skin, reduces melasma. The silk product of the invention includes, for example, a translucent glycerinated soap bar and a hard soap bar having a yellowish color and a fragrant smell.

FIELD OF THE INVENTION

The purpose of the present invention is to utilize the advantages of silk powder which is rich in amino acids and vitamin E and the mixture of silk powder with the skin cleansing product of the invention exhibiting biocidal property to assist nourishment of the skin and promote attractiveness.

BACKGROUND OF THE INVENTION

Silk powder is produced from parts of silk fibers and cocoons. It was first produced in Japan in 1987 as edible wild silk powder and subsequently was developed into a cosmetic product in 1989. The research on silk powder was first conducted in Thailand in 1997 at the Mulberry Research Center of the Department of Agriculture in Sisaket Province. This insoluble silk powder was produced from silk fibers obtained from silkworms of Nang Noi Sisaket 1 variety. According to the study, it has been found that silk powder has 16-18 amino acids. According to the research report, it has been found that this kind of silk powder has skin moisture absorption and can protect irritation from UV, thus protecting the skin from sunlight and preventing the formation of freckles and melasma on the skin. The produced silk powder was found to have many properties such as antioxidation activity and be able to destroy microorganisms that cause skin diseases. From the said properties, silk powder can be developed into healthcare products such as medicine, cosmetics and food supplements.

DETAILED DESCRIPTION OF THE INVENTION

The process for producing Thai silk soap bars comprises the steps of:

1. Preparation of Sericin Protein from Thai Silk 1.1 Silk fibers or cocoons are soaked in clean water. The ratio of silk fibers or cocoons to water is 1:20 by weight.

1.2 The materials are boiled and extracted in an autoclave at a temperature between 110-120 degrees Celsius, with pressure not exceeding 14 pounds per square inch for 25-30 minutes.

1.3 The solution is filtered by a filter having a mesh not lower than No. 220 and is concentrated, a sericin residue remains in the solution at a concentration required for use or it may be dried and sterilized prior to use for soap production.

2. Composition of Silk Cleansing Product of the Invention Comprises

1) Sericin protein from Thai silk 0.01-20.00 percent by weight.
    2) Sodium hydroxide or potassium hydroxide 2.00-20.00 percent by weight
    3) Glycerol 1.00-30.00 percent by weight (for glycerinated product) or
    4) Vegetable or animal fat 20.00-75.00 percent by weight (for hard product)
    5) Water q.s. to 100 percent by weight
    6) Fragrance trace (if any)

Method of Making a Glycerinated Soap Bar

1) The glycerol component is melted
  2) The sodium hydroxide or potassium hydroxide component is dissolved in water and heated.
  3) Sericin protein from Thai silk that has been dissolved in water and fragrance are added to (1) respectively and mixed well until a homogeneous mixture is obtained.
  4) The soap mass is solidified to take shape of a mold.

Method of Making a Hard Soap Bar

1) The vegetable or animal fats component is melted.
  2) The sodium hydroxide or potassium hydroxide component is dissolved in water and heated then slowly added to (1).
  3) Sericin protein from Thai silk that has been dissolved in water and fragrance are added to (1) respectively and mixed well until a homogeneous mixture is obtained.
  4) The soap mass is solidified to take shape of a mold.

3. Quality Inspection of Thai Silk Soap

Thai silk soap is inspected by a skin irritation test in accordance with OECD Guideline for the Testing of Chemicals, 1992, Sec. 404 Acute dermal irritation/corrosions and ISO 10993-10, 1995. Biological evaluation of medical devices-Part 10, Tests for irritation and sensitization.

Thai silk soap does not cause irritation to the skin of laboratory rabbits (when tested at a 10 percent concentration of weight per volume).

The invention claimed is:

1. A silk soap consisting of:
    (a) 0.01 to 20% by weight of sericin protein obtained from Thai silk;
    (b) 2-20% by weight of sodium hydroxide or potassium hydroxide;
    (c) about 1-30% by weight of glycerol;
    (d) optionally, a trace of fragrance; and
    (e) optionally, water to make up a balance of the soap.

2. A silk soap consisting of:
    (a) 0.01 to 20% by weight of sericin protein obtained from Thai silk;
    (b) 2-20% by weight of sodium hydroxide or potassium hydroxide;
    (c) about 20-75% by weight of vegetable or animal fat;
    (d) optionally, a trace of fragrance; and
    (e) optionally, water to make up a balance of the soap.

* * * * *